US006852901B2

(12) United States Patent
Hasenberg et al.

(10) Patent No.: US 6,852,901 B2
(45) Date of Patent: Feb. 8, 2005

(54) PROCESS TO ISOMERIZE 1-BUTENE TO 2-BUTENE

(75) Inventors: Dan M. Hasenberg, Bartlesville, OK (US); Mitchell D. Refvik, Bartlesville, OK (US); Michael S. Matson, Bartlesville, OK (US)

(73) Assignee: Chevron Phillips Chemical Company, The Woodlands, TX (US)

( * ) Notice: Subject to any disclaimer, the term of this patent is extended or adjusted under 35 U.S.C. 154(b) by 79 days.

(21) Appl. No.: 10/156,582

(22) Filed: May 28, 2002

(65) Prior Publication Data

US 2004/0106836 A1 Jun. 3, 2004

(51) Int. Cl.⁷ ................................................. C07C 5/25
(52) U.S. Cl. ...................................... 585/664; 585/906
(58) Field of Search ................................ 585/664, 660, 585/667, 669, 900

(56) References Cited

U.S. PATENT DOCUMENTS

| | | | |
|---|---|---|---|
| 2,994,727 A | | 8/1961 | Appell |
| 3,723,554 A | * | 3/1973 | Wilhelm ................. 585/482 |
| 3,723,564 A | | 3/1973 | Tidwell |
| 5,824,622 A | | 10/1998 | Harmer |
| 5,948,946 A | | 9/1999 | Harmer |

* cited by examiner

*Primary Examiner*—Thuan Dinh Dang
(74) *Attorney, Agent, or Firm*—Jenkens & Gilchrist

(57) ABSTRACT

A process is provided to produce a 2-alkene product from a 1-alkene-containing feed stream. The process comprises contacting the 1-alkene-containing feed stream in a reactor zone to isomerize the 1-alkene-containing feed stream to produce the 2-alkene product. More specifically, a process is provided to produce a 2-butene product from a 1-butene containing feed stream.

23 Claims, No Drawings

PROCESS TO ISOMERIZE 1-BUTENE TO 2-BUTENE

FIELD OF THE INVENTION

This invention relates to a novel process to isomerize an alkene-containing feed stream to produce an 2-alkene product.

Specifically, this invention relates to a novel process to isomerize 1-butene to 2-butene.

More specifically, this invention relates to a novel process to isomerize 1-butene to 2-butene by contacting a 1-butene containing feed stream with an acidized clay catalyst.

SUMMARY OF THE INVENTION

An object of this invention is to provide a process to isomerize an alkene-containing feed stream utilizing an acidized clay catalyst to produce an 2-alkene product.

Another object of this invention is to provide a process to isomerize 1-butene to 2-butene by contacting a 1-butene containing feed stream with an acidized clay catalyst.

Another object of this invention is to provide a process to isomerize 1-butene to 2-butene by contacting a 1-butene containing feed stream with an acidized clay catalyst in a flow reactor.

Another object of this invention is to provide a process to isomerize 1-butene to 2-butene by contacting a 1-butene containing feed stream with an acidized clay catalyst in a batch reactor.

In accordance with one embodiment of this invention, a process is provided to produce an 2-alkene product from an alkene-containing feed stream. The process comprises contacting the alkene-containing feed stream with an acidized clay catalyst in a reactor zone to isomerize the alkene-containing feedstream to produce the 2-alkene product.

In accordance with another embodiment of this invention, a process is provided to produce a 2-butene product from a 1-butene containing feed stream. The process comprises contacting a 1-butene containing feed stream with an acidized clay catalyst in a reactor zone to isomerize 1-butene to 2-butene.

In accordance with another embodiment of this invention, a process to produce a 2-butene product from a 1-butene containing feed stream is provided. The process comprises contacting a 1-butene containing feed stream with an acidized clay catalyst in a reactor zone to isomerize 1-butene to 2-butene;

wherein the reactor zone comprises a flow reactor;

wherein the 1-butene containing feed is dried by passing the 1-butene containing feed through a molecular sieve bed; and wherein the flow reactor is operated at a temperature between about 50° C. to about 150° C.

In accordance with another embodiment of this invention, a process is provided to produce a 2-butene product from a 1-butene containing feed stream. The process comprises contacting a 1-butene containing feed with an acidized clay catalyst in a reactor zone to isomerize 1-butene to 2-butene;

wherein the reactor zone comprises a batch reactor;

wherein the 1-butene containing feed stream is dried by passing the 1-butene containing feed through a molecular sieve bed; and wherein the batch reactor is operated at a temperature between about 95° C. to about 145° C.

These objects, and other objects, will become more apparent to others with ordinary skill in the art after reading this disclosure.

BACKGROUND OF THE INVENTION

A 2-alkene product having high purity is a product that can be utilized as a feedstock to make various other chemical compounds. There is a need in the industry to provide a process to convert an alkene-containing feed stream to a high purity 2-alkene product.

More specifically, there is a need in the chemical industry to produce a 2-butene (cis, trans, and mixed) product having a purity of about 99% for a number of reasons. The 2-butene product can be utilized to produce propylene via olefin metathesis with ethylene. High purity cis and/or trans 2-butene is also as starting materials for lubricants and agricultural chemicals.

The 1-butene containing feed stream used to produce the 2-butene product has typically been commercially available from mixed butene streams from refineries. Recently, the ability to meet the 2-butene product demand has suffered due to deterioration of the quality of available mixed butene streams. Specifically, the percentage of n-butane in the mixed butene streams has increased substantially, and the presence of this n-butane has limited the amount of 2-butene product that can be recovered via fractionation.

Generally, the mixed butene streams produced from refinery catalytic crackers are a mixture of butenes, isobutylene and butadiene. The isobutylene is usually separated from the butenes, and the 1-butene is isomerized to 2-butene prior to alkylation. Since there is about 1 to 2 wt % butadiene in these mixed butene streams, simple acid catalysis is not viable for refinery butene isomerization due to rapid coking caused by the presence of the butadiene. Phillips Petroleum Company developed and licensed the HYDRISOM® process for these refinery streams in the 1960s. The HYDRISOM® process employs an alumina catalyst with a slight loading of noble metal. A stoichiometric amount of hydrogen is simultaneously fed with the mixed butene stream, and the butadiene is selectively hydrogenated. The alumina catalyst isomerizes the 1-butene to 2-butene.

In recent years, the quality of the mixed butene streams (available from refineries and the HYDRISOM® process) has decreased markedly, and the price has risen. This change has been due to the ever increasing demand for alkylate for gasoline blending. 2-butene, when alkylated, gives an alkylate product with an octane number about 4 units higher than when 1-butene is alkylated. Since alkylate possesses high octane, is sulfur and aromatics free, and has a low vapor pressure, it has become the highest value blendstock for gasoline. Thus, the amount and purity of 2-butenes available for sale has decreased substantially.

Presently, 2-butene sells for a slight premium to 1-butene. However, thirty years ago, 1-butene sold for a slight premium to 2-butene. Furthermore, in the past 25 years, the demand for 1-butene as a comonomer for polyethylene has grown tremendously, and many companies have built ethylene oligomerization plants to meet this and other alpha olefin demand. High purity 1-butene with less than 100 ppm butadiene is now readily available at low cost providing another feedstock from which 2-butene product can be produced.

Therefore, there is a need in the chemical industry for an efficient process for isomerizing 1-butene to 2-butene. In particular, a catalyst and conditions that allow for extended catalyst run lengths (minimal catalyst deactivation) while employing an acidized clay catalyst has not been thought possible until now This invention provides a viable technology for that purpose.

Disclosure of other acidic catalysts for double bond isomerization have been reported; however, these catalysts are more expensive and less tolerant of extremes in operating conditions than the acidized clay catalysts disclosed here.

DETAILED DESCRIPTION OF THE INVENTION

In a first embodiment of this invention, a process is provided to produce an 2-alkene product from an alkene-containing feed stream. The process comprises contacting the alkene-containing feed stream with an acidized clay catalyst in a reactor zone to isomerize the alkene-containing feed stream to produce the 2-alkene product. The reactor zone comprises any type of equipment know in the art to allow isomerization. Preferably, the reactor zone comprises a batch reactor or flow reactor. Operating conditions in the reactor zone, such as temperature and pressure, are that which is sufficient to isomerize the alkene containing feed stream. Typically, the temperature is between about 50° C. and about 150° C., and the pressure is between 0 to about 600 psig.

The isomerization is accomplished by contacting the alkene-containing feed stream in a reactor zone which comprises an acidized clay catalyst. The acidized clay catalyst can be produced by any means known in the art The clay can be treated with either sulfuric acid or hydrofluoric acid. Preferably, the clay is treated with sulfuric acid. The preferred type of acidized clay catalyst is an acidized bentonite, commercially sold by Engelhard Corporation as Filtrol-24® catalyst. Generally, bentonite is comprises of about 1 to about 3% by weight crystalline silica and about 97% by weight aluminum silicate. Generally, the amount of acidized clay catalyst utilized in a batch process ranges from about 0.10 wt % to about 5.0 wt %, preferably from 0.25 wt % to 0.75 wt %.

The alkene-containing feed stream is at least one compound selected from the group consisting of hydrocarbons having from 4 to 6 carbon atoms, hydrocarbons having greater than 6 carbon atoms, and mixture thereof. Preferably, the alkene-containing feed stream has less than about 100 ppm by weight of a hydrocarbon having two double bonds, most preferably, less than 50 ppm by weight.

Optionally, the alkene-containing feed stream is dried in a drying zone. Drying in the drying zone can be accomplished by any means known in the art. For example, molecular sieve beds can be utilized to remove water. Generally, the water content of the alkene-containing feed stream is in the range of less than 50 ppm. Preferably, the water content of the alkene-containing feed stream is less than 10 ppm by weight, most preferably, less than 1 ppm by weight. It is preferred that the alkene-containing feed stream is dried to a moisture content of less than 1 ppm by weight prior to contacting with the reactor zone.

The 2-alkene product contains isomers of the compounds in the alkene-containing feed stream. The isomerization of 1-alkenes to 2-alkenes are equilibrium limited reactions. Attainment of the equilibrium limit at the lowest possible temperature is desired. When isomerizing 1-alkenes to 2-alkenes from a 1-alkene containing feed stream, the amount of 2-alkenes in the 2-alkene product is greater than about 50 wt %. Preferably, the amount of 2-alkene in the 2-alkene product is greater than about 60 wt %, most preferably, greater than 70 wt %.

In addition, it is preferred that little or no skeletal isomerization of the alkene feed occurs during the double bond isomerization process. Preferably, less than 3% skeletal isomerization occurs, and most preferably less than 0.4% skeletal isomerization occurs.

In a second embodiment of this invention, a process to produce a 2-butene product from a 1-butene containing feed stream is provided. The process comprises contacting a 1-butene containing feed stream with an acidized clay catalyst in a reactor zone to isomerize 1-butene to produce a 2-butene product.

The isomerization is accomplished by contacting the 1-butene containing feed stream in a reactor zone which comprises the acidized clay catalyst. The acidized clay was discussed previously in this disclosure. Generally, the weight hourly space velocity (weight of feed/weight of catalyst-hr, WHSV) through the reactor zone is between about 0.25 and about 10. Preferably, the WHSV is between about 1.0 and about 3.0, and most preferably, the WHSV is 2.

The pressure in the reactor zone is in a range of 0 psig to about 600 psig. Preferably, the pressure is in a range of about 10 psig to about 200 psig, most preferably, 25 psig to 60 psig. The temperature of the reactor zone is in a range of about 50° C. to about 150° C. Preferably, the temperature is in a range of about 80° C. to about 145° C., most preferably, between 110° C. to 150° C.

Generally, the 1-butene content in the 1-butene containing feed stream is greater than about 70 wt %, preferably greater than about 80 wt %, and most preferably, greater than 90 wt %. When isomerizing 1-butene to 2-butene from a 1-butene containing feed stream, the amount of 2-butene in the 2 butene product is greater than about 50 wt %. Preferably, the amount of 2-butene in the 2-butene product is greater than about 60 wt %, most preferably, greater than 70 wt %.

Optionally, the 1-butene containing feed stream is dried in a drying zone. Drying in the drying zone can be accomplished by any means known in the art. For example, molecular sieve beds can be utilized to remove water. Generally, the water content of the 1-butene containing feed stream is in the range of less than 50 ppm. Preferably, the water content of the 1-butene containing feed stream is less than 10 ppm by weight, most preferably, less than 1 ppm by weight.

EXAMPLES

The following examples are provided to assist a person skilled in the art with further illustrations of this invention. These examples are intended to be illustrative of the invention but are not meant to be construed as limiting the reasonable scope of the invention.

Example 1

Laboratory Flow Reactor Run 1

In a laboratory reactor, a dry 1-butene containing feed was contacted with a Filtrol-24® catalyst obtained from Engelhard Corporation. 31 grams of Filtrol-24® catalyst were utilized. The reactor was operated at 500 psig. The 1-butene containing feed was contacted with the Filtrol-24® catalyst at a WHSV at each temperature specified in Table I. The results also are tabulated in Table I.

TABLE I

| Temperature (°C.) | WHSV[1] | 1-Butene (wt %) | 2-Butene (wt %) | Octenes (wt %) | Dodecenes (wt %) | Isobutylene (wt %) |
|---|---|---|---|---|---|---|
| 24 | 2 | 92.2 | 4.7 | 0.9 | 0 | 0.0 |
| 50 | 2 | 81.3 | 14.7 | 0.6 | 0 | 0.4 |
| 75 | 2 | 53.9 | 43.4 | 0.4 | 0 | 0.4 |
| 100 | 2 | 22.3 | 74.0 | 0.2 | 0 | 0.3 |
| 121 | 2 | 9.2 | 81.3 | 0.3 | 0 | 0.2 |
| 150 | 2 | 7.5 | 84.2 | 1.7 | 0 | 0.2 |
| 179 | 2 | 3.5 | 42.6 | 41.6 | 6.2 | 0.3 |
| 201 | 2 | 3.5 | 35.3 | 42.8 | 6.8 | 0.7 |
| 225 | 2 | 1.1 | 16.3 | 55.0 | 13.3 | 1.6 |
| 250 | 2 | 0 | 4.2 | 53.0 | 14.3 | 2.6 |

[1]WHSV - weight hour space velocity, weight feed/(weight catalyst-hr)

From these data, it can be seen that the optimum temperature in a flow reactor containing Filtrol-24® catalyst is between 110° C. and 150° C.

Example 2

Laboratory Flow Reactor Run 2

In a larger laboratory flow reactor, a dry 1-butene containing feed was further dried using Type 3A mole sieves obtained from UOP. The dry 1-butene containing feed was then contacted with a Filtrol-24® catalyst obtained from Engelhard. 672 grams of Filtrol-24® catalyst were utilized. The reactor was operated at 450 psig. The 1-butene containing feed was contacted with the Filtrol-24® catalyst at a WHSV of 2. The results are tabulated in Table II.

TABLE II

| WAT[1] °C. | Time (hours) | 1-butene wt % | trans 2-butene wt % | cis 2-butene wt % | C8's wt % | C12's wt % | trans/cis ratio |
|---|---|---|---|---|---|---|---|
| 24 | 0 | | | | | | |
| 78 | 7 | 18.4 | 45.70 | 32.10 | 3.75 | 0.00 | 1.42 |
| 113 | 15 | 9 | 55.10 | 30.60 | 5.20 | 0.08 | 1.80 |
| 128 | 20 | 8.6 | 55.30 | 29.70 | 6.20 | 0.12 | 1.86 |
| 120 | 31 | 8.9 | 55.00 | 30.60 | 4.80 | 0.09 | 1.80 |
| 126 | 37 | 9 | 55.50 | 30.10 | 5.30 | 0.06 | 1.84 |
| 121 | 42 | 9.2 | 54.90 | 31.90 | 3.90 | 0.06 | 1.72 |
| 114 | 53 | 8.8 | 51.30 | 30.35 | 8.10 | 0.20 | 1.69 |
| 102 | 61 | 14.2 | 49.00 | 34.00 | 2.30 | 0.02 | 1.44 |
| 114 | 72 | 10 | 52.60 | 30.40 | 6.37 | 0.08 | 1.73 |
| 100 | 74 | 9.17 | 43.78 | 27.64 | 18.93 | 0.05 | 1.58 |
| 103 | 80 | 13.2 | 50.30 | 33.40 | 3.09 | 0.07 | 1.51 |
| 81 | 88 | 37.6 | 33.40 | 28.07 | 0.98 | 0.00 | 1.19 |
| 76 | 97 | 38.23 | 33.07 | 26.45 | 1.56 | 0.00 | 1.25 |
| 108 | 104 | 12.1 | 50.65 | 31.56 | 5.13 | 0.10 | 1.60 |
| 108 | 120 | 14.3 | 48.40 | 32.27 | 4.56 | 0.11 | 1.50 |
| 100 | 134 | 14.3 | 48.40 | 32.30 | 4.60 | 0.11 | 1.50 |
| 108 | 137 | 19.33 | 44.73 | 31.88 | 3.60 | 0.06 | 1.40 |
| 123 | 145 | 9.81 | 53.08 | 30.16 | 6.80 | 0.18 | 1.76 |
| 135 | 158 | 8.6 | 54.00 | 28.00 | 9.70 | 0.16 | 1.93 |
| 119 | 165 | 9.8 | 53.30 | 32.05 | 4.70 | 0.09 | 1.66 |
| 80 | 200 | 26.6 | 39.40 | 30.50 | 3.30 | 0.04 | 1.29 |
| 125 | 211 | 8.26 | 38.55 | 20.60 | 29.90 | 2.09 | 1.87 |
| 113 | 234 | 8.3 | 50.10 | 27.70 | 13.30 | 0.60 | 1.81 |
| 137 | 237 | 7.4 | 38.10 | 20.30 | 31.15 | 2.27 | 1.88 |

[1]WAT, weight average temperature defined as (inlet temperature + outlet temperature)/ 2.

There was no detectable formation of isobutylene in any of the run 2 reactor effluent samples. The detection limit utilizing gas chromatography was 0.2 wt %.

From these data, it can be seen that the optimum temperature in a flow reactor containing Filtrol-24® catalyst is between 110° C. and 150° C.

In addition, there was no measurable catalyst deactivation during the course of this experiment (237 hours on-stream). This demonstrates that it is possible to have consistent operation with little or no catalyst deactivation of the acidic clay catalyst during isomerization of 1-butene to 2-butene.

That which is claimed is:

1. A process to produce a 2-alkene product from a 1-alkene-containing feed stream, said process comprising contacting said 1-alkene-containing feed stream with catalyst consisting essentially of an acidized clay in a reactor zone to isomerize said 1-alkene-containing feed stream to produce said 2-alkene product.

2. A process according to claim 1 wherein said reactor zone comprises a batch reactor.

3. A process according to claim 2 wherein said batch reactor temperature is between about 50° C. and about 150° C.

4. A process according to claim 1 wherein said reactor zone comprises a flow reactor.

5. A process according to claim 4 wherein said flow reactor is operated at a temperature between about 50° C. and about 150° C.

6. A process according to claim 1 wherein said catalyst is produced by treating clay with sulfuric acid.

7. A process according to claim 4 wherein said flow reactor is operated at a space velocity (WHSV) between about 0.25 and about 10.

8. A process according to claim 1 wherein said alkene-containing feed stream is dried utilizing a molecular sieve bed to reduce the moisture content to less than 50 ppmw.

9. A process according to claim 2 wherein said batch reactor is operated with a batch time between about 1 to about 8 hours.

10. A process to produce a 2-butene product from a 1-butane-containing feed stream, said process comprising contacting a 1-butene-containing feed stream with an catalyst consisting essentially of an acidized clay in a reactor zone to isomerize 1-butene to produce a 2-butene product.

11. A process according to claim 10 wherein said reactor zone comprises a batch reactor.

12. A process according to claim 11 wherein said batch reactor temperature is between about 50° C. and about 150° C.

13. A process according to claim 10 wherein said reactor zone comprises a flow reactor.

14. A process according to claim 13 wherein said flow reactor is operated at a temperature between about 50° C. and about 150° C.

15. A process according to claim 10 wherein said catalyst is produced by contacting clay with sulfuric acid.

16. A process according to claim 13 wherein said flow reactor is operated at a space velocity (WHSV) between about 0.25 and about 10.

17. A process according to claim 10 wherein said 1-butene containing feed stream is dried utilizing a molecular sieve bed to reduce the moisture content to less than 50 ppmw.

18. A process to produce a 2-butene product from a 1-butene containing feed stream comprising contacting a 1-butene containing feed stream with an catalyst consisting essentially of an acidized clay in a reactor zone to isomerize 1-butene to produce a 2-butene product;
   wherein said reactor zone comprises a flow reactor;
   wherein said 1-butene containing feed stream is dried utilizing a molecular sieve bed; and
   wherein said flow reactor is operated at a temperature between about 50° C. and about 150° C.

19. A process to produce a 2-butene product from a 1-butene containing feed stream comprising contacting a 1-butene containing feed stream with an catalyst consisting essentially of an acidized clay in a reactor zone to isomerize 1-butene to produce said 2-butene product;

wherein said reactor zone comprises a batch reactor;

wherein said 1-butene containing feed stream is dried utilizing a molecular sieve bed; and wherein said batch reactor is operated at a temperature between about 105° C. and about 145° C.

20. A process according to any one of claim 10, 18 or 19 wherein the isobutylene content in the 2-butene product is below about 0.4 wt % and the temperature in the reactor or reactor zone is less than 150° C.

21. A process according to any one of claim 10, 18 or 19 wherein said 1-butene containing feed stream has a diolefin content between about 50 and about 100 ppm.

22. A process according to claim 1 wherein said 1-alkene containing feed stream has a diolefin content between about 50 and about 100 ppm.

23. A process according to any one of claim 1, 10, 18, or 19 wherein acid clay catalyst deactivation occurs after about 230 hours of operation.

* * * * *